US007615342B2

(12) United States Patent  
North

(10) Patent No.: US 7,615,342 B2  
(45) Date of Patent: Nov. 10, 2009

(54) ACTN3 GENOTYPE SCREEN FOR ATHLETIC PERFORMANCE

(75) Inventor: Kathryn Nance North, Glebe (AU)

(73) Assignee: Genetic Technologies Limited, Fitzroy (AU)

( * ) Notice: Subject to any disclaimer, the term of this patent is extended or adjusted under 35 U.S.C. 154(b) by 82 days.

(21) Appl. No.: 10/527,831

(22) PCT Filed: Sep. 15, 2003

(86) PCT No.: PCT/AU03/01202

§ 371 (c)(1),  
(2), (4) Date: Jan. 9, 2006

(87) PCT Pub. No.: WO2004/024947

PCT Pub. Date: Mar. 25, 2004

(65) Prior Publication Data

US 2006/0121478 A1 Jun. 8, 2006

(30) Foreign Application Priority Data

Sep. 16, 2002 (AU) .............................. 2002951411

(51) Int. Cl.  
*C12Q 1/68* (2006.01)  
*C07H 21/04* (2006.01)  
*C12P 19/34* (2006.01)

(52) U.S. Cl. .......................... 435/6; 536/24.3; 435/91.2

(58) Field of Classification Search .................... 435/6; 536/24.3  
See application file for complete search history.

(56) References Cited

U.S. PATENT DOCUMENTS

| 801,274 | A | 10/1905 | Schulz |
| 4,683,195 | A | 7/1987 | Mullis et al. |
| 4,683,202 | A | 7/1987 | Mullis |
| 4,800,159 | A | 1/1989 | Mullis et al. |
| 4,883,750 | A | 11/1989 | Whiteley et al. |
| 5,206,347 | A | 4/1993 | Ruoslahti et al. |
| 5,279,721 | A | 1/1994 | Schmid |
| 5,919,626 | A | 7/1999 | Shi et al. |
| 5,952,174 | A | 9/1999 | Nikiforov et al. |

FOREIGN PATENT DOCUMENTS

| EP | 0320308 B1 | 11/1993 |
| EP | 0329822 B1 | 6/1994 |
| GB | 2 202 328 A | 9/1988 |
| WO | WO 88/10315 | 12/1988 |
| WO | WO 89/06700 | 7/1989 |
| WO | WO 89/09284 | 10/1989 |

OTHER PUBLICATIONS

North et al, Nature Genetics (1999) vol. 21, pp. 353-354.*
Lucia, et alInternational Journal of Sports Medicine(2006) vol. 27, pp. 880-884.*
North Nature Genetics (1999) vol. 21 pp. 353-354.*
Costill et al Journal of Applied Physiology (1976) vol. 40, pp. 149-153.*
Rankinen et al, Medicine in sports and Exercise (2002) pp. 1219-2133.*
Voet et al Biochemistry, published 199, p. 78.*
Brenner et al (Trends in Genetics (2001) vol. 17, pp. 414-418).*
O'Brien et al (Science magazine (1999) vol. 286, pp. 458-462, 479-481.*
Pitsiladis et al (Lancet (2005) vol. 366, pp. s16-s17).*
Mills et al, Human Molecular Genetics (2001) vol. 10, pp. 1335-1346.*
genecards.org/cgi-bin/carddisp.pl?gene=ACTN3&search=actn3&suff=txt, pp. 1-11, Mar. 24, 2007.*
Yang, et al, Med. Sci. Sport and Exercise (2005) vol. 37, s42.*
Moran et al, European Journal of Human Genetics (2007) vol. 15, pp. 88-93.*
Blanchard, Andrew, et al., "The Structure and function of a-actinin," Journal of Muscle Research and Cell Motility 10, 280-289 (1989).
Beggs, Alan H., et al., "Cloning and Characterization of Two Human Skeletal Muscle a-Actinin Genes Located on Chromosomes 1 and 11" The Journal of Biological Chemistry, vol. 267, No. 13, Issue of May 5, pp. 9281-9288, 1992.
Nave, Rudiger, et al., "Interaction of a-actinin and nebulin In vitro," Elsevier Science Publishers, vol. 269, No. 1, 163-166, Aug. 1990.
Pap, Iris, et al., "Alpha actinin-CapZ, an anchoring complex for thin filaments in Z-line," Journal of Muscle Research and Cell Motility 20, pp. 187-197, 1999 Kluwer Academic Publishers.
Salmikangas, Paula, et al., "Myotilin, a novel sarcomeric protein with two Ig-like domains, is encoded by a candidate gene for limb-girdle muscular dystrophy," Human Molecular Genetics, 1999, vol. 8, No. 7, pp. 1329-1336 1999 Oxford University Press.
Bellin, Robert M., et al., "Molecular characteristics and Interactions of the Intermediate Filament Protein Synemin," The Journal of Biologlcal Chemistry, vol. 274, No. 41, Issue of Oct. 8, pp. 29493-29499.
McGregor, Alistair, "Identification of the Vinculin-binding Site in the Cytoskeletal Protein a-actinin" Biochem (1994) 301, pp. 225-233 (Printed in Great Britain).

(Continued)

*Primary Examiner*—Sarae Bausch  
*Assistant Examiner*—Steven C Pohnert  
(74) *Attorney, Agent, or Firm*—Sheridan Ross P.C.

(57) ABSTRACT

The present invention concerns novel methods of selecting or matching a sport or sporting event to an individual (e.g. a sprint/power sport or an endurance sport) and predicting athletic performance, the methods involving assessing ACTN3 genotype. In alternative embodiments, training regimens may be optimally designed for athletes by assessing the ACTN3 genotypes. Certain embodiments concern combining the assessment of the ACTN3 genotype with other known fitness-related genes to better assess the athletic potential of an individual. In addition, the genotypic analysis of the ACTN3 gene may be combined with physiological tests, physical measurements and/or psychological assessments to more optimally design a training regimen for an individual athlete.

14 Claims, 1 Drawing Sheet

OTHER PUBLICATIONS

Hance, Jacqueline, "a-Actinin-2 Is a New Component of the Dystrophin-Glycoprotein Complex" Archihves of Biochemistry and Biophysics, vol. 365, No. 2, May 15, pp. 216-222, 1999.

Otey, Carol A., et al., "Mapping of the a-Actinin Binding Site within the B1 Integrin Cytoplasmic Domain," The Journal of Biological Chemistry, vol. 268, No. 28, Issue of Oct. 5, pp. 21193-21197.

Fukami, et al., "a-Actinin and Vinculin Are PIP2-binding Proteins Involved in Signaling by Tyrosine Kinase" The Journal of Biological Chemistry, vol. 269, No. 2, Issue of Jan. 14, pp. 1518-1522, 1994.

Shibasaki, Futoshi, et al., "Phosphatidylinositol 3-kinase binds to a-actinin through the p85 subunit" Biochem Journal (1994) 302, pp. 551-557 (Printed In Great Britain).

Pomies, Pascal, et al., "CRP1, a LIM Domain Protein Implicated in Muscle Differentiation, Interacts with a-Actinin" The Journal of Cell Biology, vol. 139, No. 1, Oct. 6, 1997, pp. 157-168.

Pomies, Pascal, et al., "Purification and Characterization of an a-Actinin-Binding PDZ-LiM Protein that is Up-regulated during Muscle Differentiation" The Journal of Biological Chemistry, 1999 the The American Society for Biochemistry and Molecular Biology, Inc., vol. 274, No. 41, Issue of Oct. 8, 1999, pp. 29242-29250.

North, Kathryn, et al., "A common nonsense mutation results in a-actinin-3 deficiency in the general population" 1999 Nature America Inc., vol. 21, Apr. 1999, pp. 353-354.

Nowak, Martin A, et al., "Evolution of genetic redundancy" Letters to Nature vol. 388 Jul. 10, 1997, pp. 167-171.

Chan, Yiu-Mo, et al., "Human Skeletal Muscle-Specific a-Actinin-2 and-3 Isoforms Form Homodimers and Heterodimers in Vitro and In Vivo" Biochemical and Biophysical Research Communications 248, 1998 Article No. RC 988920, pp. 134-139.

Rieder, Mark J., "Sequence variation in the Human Anglotensin Converting Enzyme" Nature Genetics, vol. 22, May 1999, pp. 59-62.

Gayagay, George, et al., "Elite Endurance Athletes and the ACE I allele—the role of Genes in Athletic Performance" Hum Genet (1998) 103 pp. 48-50.

Montgomery, H. E., et al. "Human Gene for Physical Performance" scientific correspondence Nature Macmillan Publishers Ltd 1998 vol. 393 May 21, 1998, pp. 221-222.

Myerson, Saul, et al. "Human Angiotensin I-converting enzyme gene and Endurance Performance" The American Physiological Society 1999 8750-7587/99, pp. 1313-1316.

Nazarov, Igor B., et al. "The angiotensin Converting Enzyme I/D polymorphism in Russian athletes" European Journal of Human Genetics (2001) 9, pp. 797-801.

Woods, David, et al., "Elite Swimmers and the D allele of the ACE I/D Polymorphism" Hum Genet (2001) 108, pp. 230-232.

Meltzoff, A., "Rational Imitation in Preverbal Infants" Nature, vol. 415, Feb. 14, 2002, pp. 755-756.

Rankinen, Tuomo, et al., "The Human Gene Map for Performance and Health-related Fitness Phenotypes: the 2001 update" MSSE Special Report, 0195-9131/02/3408-1219, 2002 by the American College of Sports Medicine.

Perusse, Louis, et al., "The Human Gene Map for Performance and Health-related Fitness Phenotypes: The 2002 Update," Medicine & Science in Sports & Exercise, the American College of Sports Medicine 0195-9131/03/3508 pp. 1248-1264.

Mills, Michelle, et al., "Differential expression of actin-binding proteins, a-actinin-2 and-3, In different species: implications for the evolution of functional redundancy" Human Molecular Genetics, vol. 10, No. 13, pp. 1335-1346.

Eizema, Karin, et al., "Differential Expression of Equine Myosin Heavy-chain mRNA and Protein Isoforms in a Limb Muscle" vol. 51(9): The Journal of Histochemistry & Cytochemistry, 2003, pp. 1207-1216.

Walker, G. Terrance, et al., "Isothermal in vitro amplification of DNA by a Restriction enzyme/DNA Polymerase System" vol. 89, pp. 392-396, Jan. 1992 Applied Biological Sciences, pp. 392-396.

Kwoh, D. Y., et al., "Transcription-based amplification system and detection of amplified human immunodeficiency virus type 1 with a bead-based sandwich hybridization format" Biochemistry, Proc. Natl. Acad. Sci. USA, vol. 86, pp. 1173-1177, Feb. 1989.

Ohara, Osamu, et al., "One-sided Polymerase Chain Reaction: The amplification of cDNA" Pro. Natl. Acad. Sci. USA, Biochemistry, vol. 86, pp. 5673-5677, Aug. 1989.

North, Kathryn N., et al., "Deficiency of a Skeletal Muscle Isoform of a-Actinin (a-Actinin-3) in Merosin-Positive Congenital Muscular Dystrophy" Neuromusc. Disord., vol. 6, No. 4, pp. 229-235, 1996.

Friden, J., et al., "Eccentric Exercise-Induced Injuries to Contractile and Cytoskeletal Muscle Fibre components" Acta Physiol Scand 2001, 171, Scandinavian Physiological Society, pp.321-326.

"Deficiency of α-Actinin-3 (ACTN3) Occurs in Different Forms of Muscular Dystrophy" by Vainzof et al., Neuropediatrics 28 (1997), 223-228.

"ACTN3 Genotype is Associated with Human Elite Athletic Performance" by Yang et al., American Journal of Human Genetics, 73: 627-631, 2003.

"Differential Expression of the Actin-Binding Proteins, α-actinin-2 and-3, in Different Species: Implications for the Evolution of Functional Redundancy" by Mills, et al., Human Molecular Genetics, 2001, vol. 10, No. 13, 1335-1346.

"Deficiency of Muscle α-Actinin-3 is Compatible with High Muscle Performance" BY Zanoteli et al., Journal of Molecular Neuroscience, vol. 20, 2003, pp. 39-42.

"A Common Nonsense Mutation Results in α-Actinin-3 Deficiency in the General Population" by North et al., Nature Genetics, vol. 21, Apr. 1999, pp. 353-354.

Nazarov, Igor B., et al., "The angiotensin converting enzyme I/D polymorphism in Russian athletes" European Journal of Human Genetics (2001) 9, 797-801 XP-002404827.

Niemi, et al., "Mitochondrial DNA and ACTN3 genotypes in Finnish elite endurance and sprint athletes," European Journal of Human Genetics, vol. 13, pp. 965-969, 2005.

Druzhevskaya et al., "Association of the ACTN3 R577X Polymorphism with Power Athlete Status in Russians", Eur J Appl Phsiol, 2008, 103:631-634.

Delmonico, et al., "Alpha-Actinin-3 (ACTN3) R577X Polymorphism Influences Knee Extensor Peak Power Response to Strength Training in Older Men and Women", Journal of Gerontology: Medical Sciences, 2007, vol. 62A, No. 2, 2006-212.

Yang et al., "ACTN3 Genotype Is Associated with Human Elite Athletic Performance", Am. J. Hum. Genet., 2003, 73:627-631.

* cited by examiner

SEQUENCE LISTING

<160> NUMBER OF SEQ ID NOS: 2

<210> SEQ ID NO 1
<211> LENGTH: 21
<212> TYPE: DNA
<213> ORGANISM: Homo sapiens

<400> SEQUENCE: 1
ctgttgcctg tggtaagtgg g    21

<210> SEQ ID NO 2
<211> LENGTH: 21
<212> TYPE: DNA
<213> ORGANISM: Homo sapiens

<400> SEQUENCE: 2
tggtcacagt atgcaggagg g    21

ACTN3 GENOTYPE SCREEN FOR ATHLETIC PERFORMANCE

CROSS-REFERENCE TO RELATED APPLICATIONS

This application claims the benefit of PCT Application No. PCT/2003/001202 (WO 2004/024947 A1) filed Sep. 15, 2003 which claims benefit to Australian Provisional Patent Application No. 2002941411 filed Sep. 14, 2002. Said application are incorporated herein by reference.

BACKGROUND OF THE INVENTION

1. Field of the Invention

The present invention relates to methods for selecting or matching a sport or sporting event to an individual (e.g., a sprint/power sport or an endurance sport) to increase their chances of success, optimizing the training programs of individuals, and for predicting the athletic performance of individuals. Certain embodiments of the invention relate to identifying specific gene(s) or alterations in the gene(s) that correlate with potential athletic performance. More particularly, the invention relates to methods of genotyping an individual with respect to the gene encoding the skeletal muscle protein, α-actinin-3 (ACTN3). In a specific embodiment, the ACTN3 genotype is determined for a single nucleotide polymorphism (SNP) site 1747 C>T.

2. Description of Related Art

In an increasingly competitive environment for athletic performance, talent search programs are on the rise to ensure that those with the potential to become an elite athlete are identified earlier in life to enable a head start in their efforts to reach their peak performance. These talent search programs are presently based on actual performance data and phenotypic predictors determined by the type of training to be undertaken, as well as the likely demands from the particular sport. One weakness of both current training programs and talent search criteria is the inability to determine whether an individual has already reached his/her performance potential, and so is unlikely to respond optimally to further training.

Another weakness of the current talent search programs, which is particularly relevant in countries with a relatively small population base in a large geographic area, is the opportunity for selection. An individual brought up in a environment with widespread access to sporting and coaching facilities is more likely to achieve success, and therefore more likely to come to the attention of coaches and talent scouts than a young individual with potential who resides in a relatively isolated location or who might otherwise have an underprivileged background. Similarly, individuals with potential to excel in lower profile sports such as rowing may be overlooked simply because these sports programs are less available in most schools. Again, this diminishes the chances of early identification and participation, leading to subsequent overlook by coaches and talent scouts. These are dilemmas facing sporting organizations such as the Australian Institute of Sport (AIS), since potential elite athletes are preferably selected and inducted into relevant training programs at a young age.

The possibility exists that linkages or associations of genotype or genotypic markers to certain physiological traits may contribute to or reduce performance in an elite athlete. Such methods may permit the development of DNA screens to assist in the selection of individuals with elite athlete potential. Such screens may help in overcoming some of the selection limitations of current talent search programs. In addition, such screening methods may assist in recognizing to whom and when a possibly small, but critical difference in an individual's training program should be made.

The α-actinins are a family of actin-binding proteins related to dystrophin and the spectrins (Blanchard, A. et al., *Journal of Muscle Research & Cell Motility*, 10, 280-289, 1989). In skeletal muscle, the family members α-actinin-2 and α-actinin-3 are major structural components of sarcomeric Z-lines, where they function to anchor actin-containing thin filaments in a constitutive manner (Beggs, A. H. et al., *Journal of Biological Chemistry*, 267, 9281-9288, 1992). However, recent studies suggest additional roles for the α-actinins in skeletal muscle.

It has been found that sarcomeric α-actinins bind to other thin filament and Z-line proteins including nebulin, myotilin, CapZ and myozenin (Nave, R. et al., *FEBS Letters*, 269, 163-166, 1990, Papa, I. et al., *Journal of Muscle Research & Cell Motility*, 20, 187-197, 1999, and Salmikangas, P. et al., *Human Molecular Genetics*, 8, 1329-1336, 1999), the intermediate filament proteins, synemin and vinculin (Bellin, R. M. et al., *Journal of Biological Chemistry*, 274, 29493-29499, 1999, and McGregor, A. et al., *Biochemical Journal*, 301, 225-233, 1994), and the sarcolemmal membrane proteins, dystrophin and β1 integrin (Hance, J. E. et al., *Archives of Biochemistry & Biophysics*, 365, 216-222, 1999, and Otey, C. A. et al., *Journal of Biological Chemistry*, 268, 21193-21197, 1993). These binding studies suggest that the α-actinins play a role in thin filament organization and the interaction between the sarcomere cytoskeleton and the muscle membrane. In addition, sarcomeric α-actinin binds phosphatidylinositol 4,5-bisphophate (Fukami, K. et al., *Journal of Biological Chemistry*, 269, 1518-1522, 1994), phosphatidylinositol 3 kinase (Shibasaki, F. et al., *Biochemical Journal*, 302, 551-557, 1994) and PDZ-LIM adaptor proteins (Pomies, P. et al., Journal of Cell Biology, 139, 157-168, 1997, and Pomies, P. et al., *Journal of Biological Chemistry*, 274, 29242-29250), suggesting a role in the regulation of myofiber differentiation and/or contraction.

In humans, the α-actinin-2 gene, ACTN2, is expressed in all skeletal muscle fibers, while expression of ACTN3, encoding α-actinin-3, is limited to a subset of type 2 (fast) fibers (North, K. N. et al., *Nature Genetics*, 21, 353-354, 1999). It has been recently demonstrated that α-actinin-3 is absent in ~18% of individuals in a range of human populations and that homozygosity for a premature stop codon (577X) accounts for all cases of true α-actinin-3 deficiency states identified to date. An additional polymorphism (523R) occurs in linkage disequilibrium with 577X, but does not appear to exert a deleterious effect when expressed in the heterozygous state in coupling with 577R. Further, absence of α-actinin-3 is not associated with an obvious disease phenotype, suggesting that ACTN3 is redundant in humans (North, K. N. et al., 1999 Nature Genetics 21: 353-354).

Functional redundancy occurs when two genes perform overlapping functions so that inactivation of one of the genes has little or no effect on the phenotype (reviewed in Nowak, M. A. et al., *Nature*, 388, 167-171, 1997). In human skeletal muscle, α-actinin-2 expression completely overlaps α-actinin-3. ACTN2 and ACTN3 are also 80% identical and 90% similar (Beggs, A. H. et al., 1992, supra), and α-actinin-2 and α-actinin-3 are capable of forming heterodimers in vitro and in vivo, suggesting structural similarity and lack of significant functional differences between the two skeletal muscle α-actinin isoforms (Chan, Y. et al., *Biochemical & Biophysical Research Communications*, 248, 134-139, 1998). It is hypothesised that α-actinin-2 is able to compensate for the absence of α-actinin-3 in type 2 (fast) fibers in humans.

SUMMARY OF THE INVENTION

Despite the apparent functional redundancy of ACTN3 and ACTN2 in humans, genotype screens of a pool of elite Australian athletes and noted Caucasian sprint athletes (particularly short distance runners, swimmers and cyclists) showed a very low frequency of homozygosity for the ACTN3 premature stop codon 577X mutation (i.e. an ACTN3 null mutation, 577XX) relative to the Australian Caucasian population at large. It is therefore considered that screening for ACTN3 genotype, would provide considerable assistance in the selection of young individuals with potential for elite performance in sprint-type sports and events. Also, the genotype screens showed that the frequency of the 577XX genotype was reatlively higher in Caucasian elite endurance athletes. Thus, a screening procedure for ACTN3 577XX genotype, may also provide assistance in identifying young individuals with potential for elite performance in endurance sports and events.

The present invention solves a need in the art by providing in vitro methods for screening individuals for athletic potential. In a one embodiment, the genotype of an individual may be determined for the gene ACTN3. In another embodiment, mRNA or protein is isolated from type 2 skeletal muscle and analyzed for the presence or absence of ACTN3. In another embodiment, individuals are identified by isolating, DNA from blood or buccal swab samples and the DNA is amplified and analyzed for the presence or absence of a premature stop codon (577X) in the ACTN3 gene. Other embodiments provide methods for screening individuals for athletic potential by combining the screening of ACTN3 with other genetic or physiological tests. In addition, the methods described provide for developing training program(s) better suited for an individual athlete by genetic assessments, physiological tests, physical measurements and/or psychological assessments.

In another embodiment, the invention provides for screening individuals for elite athletic potential, the method for example is carried out by obtaining a suitable muscle cell sample from an individual and detecting in the sample, α-actinin-3 protein and/or messenger RNA encoding that protein.

Particular embodiments of the invention relate to a method of predicting the presence or absence of a particular phenotype. The method comprises obtaining a nucleic acid sample from an individual and determining the identity of one or more bases (nucleotides) at specific (e.g., polymorphic) sites of nucleic acid molecules described herein, wherein the presence of a particular base at that site is correlated with a specified phenotype, thereby predicting the presence, absence, or likelihood of the presence or absence, of the phenotype in the individual.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

Figure 1:
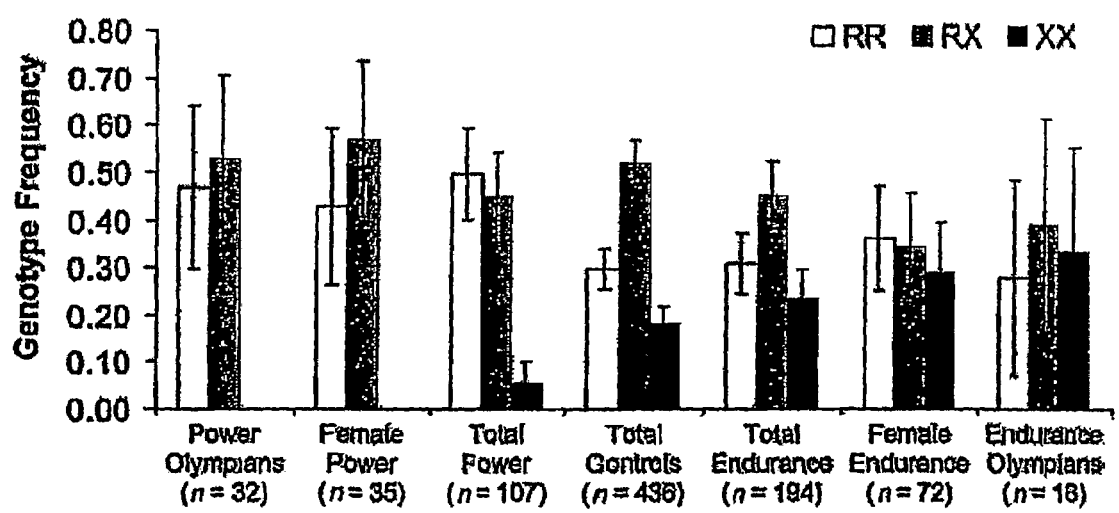
FIG. 1 illustrates the ACTN3 genotype frequency in controls, elite sprint/power athletes and elite endurance athletes.

TABLE 1: represents the genotypes of the R577X SNP in ACTN3 in Caucasian elite athletes of specific disciplines.

TABLE 2 represents a summary of individuals tested for number and frequency (%) of ACTN3 alleles in controls and elite sprint/power and endurance athletes.

TABLE 3 represents SNPs identified in the ACTN3 gene thus far and compiled in a list from the NCBI SNP website.

TABLE 4 represents symbols, full names, and cytogenic location of nuclear and mitochondrial genes of the 2002 Human Gene Map for Performance and Health-Related Fitness Phenotypes.

TABLE 5 represents endurance phenotypes and case-control studies (DNA polymorphisms).

TABLE 6 represents genotype and allele frequencies of ACTN3 577/R/X alleles in human populations.

Definitions

As used herein in the specification, "a" or "an" may mean one or more. As used herein in the claim(s), when used in conjunction with the word "comprising", the words "a" or "an" may mean one or more than one. As used herein "another" may mean at least a second or more.

"Elite athlete" or variants thereof, refers to athletes that perform at the very highest levels in terms of endurance, speed and/or strength (e.g. such that they are capable of competing at State, National and/or International levels in their sport).

As used herein, the terms "SNPs" or "single nucleotide polymorphisms" refer to single base changes at a specific location in an organism's (e.g., a human) genome.

DETAILED DESCRIPTION

In the following section, several embodiments of, for example, methods are described in order to exemplify various embodiments of the invention. It will be obvious though, to one skilled in the art that practicing the various embodiments does not require the employment of all or even some of the specific details outlined herein. In some cases, well known methods or components have not been included in the description.

Methods and compositions to screen individuals for athletic potential are disclosed. In one embodiment of the invention, a method to screen individuals for the presence or absence of ACTN3 protein and/or mRNA is disclosed. In another embodiment of the invention, a method to screen individuals for the presence or absence of ACTN3 genotype variations is disclosed. In another embodiment of the invention, a method to screen individuals for the presence or absence of particular ACTN3 genotypes, such as 577RR, 577XR or 577XX is disclosed. Identification of ACTN3 protein may be accomplished by directly measuring the protein levels or by indirectly measuring protein levels (e.g. antibodies etc).

ACTN3 Polymorphisms and Other Genetic Variations

A common polymorphism in humans has been identified in the gene encoding the skeletal muscle protein, α-actinin 3 (ACTN3) that is only present in type 2 (fast) fibers. Three possible genotypes 577RR (wildtype—expresses α-actinin-3), 577RX (heterozygous—.alpha. -actinin-3 present), and 577XX (homozygous null—no -.alpha.-actinin-3 in skeletal muscle), have been identified. The allelic frequency varies in different ethnic groups (i.e. about 18% of Caucasians are .alpha. -actinin-3 deficient compared to .about. 1% of African Zulus) (see Table 6west Africans and African Americans). As discussed in the Examples below, in Caucasian elite sprint/power athletes, the frequency of the 577RR genotype is very low. Thus a screening procedure for ACTN3 577XX genotype, may provide assistance in identifying for example young Caucasian individuals with potential for elite performance in sprint or power-type sports and events. In contrast, in Caucasian elite endurance athletes, the frequency of the 577XX genotype is relatively higher. Thus a screening procedure for ACTN3 577XX genotype, may also provide assistance in identifying for example young Caucasian individuals with potential for elite performance in endurance sports and events. In addition, Table 6 illustrates the genotype and allele frequencies of ACTN3 577R/X alleles in different human populations. In Table 6 and Table 2, the negroid Africans (ie Zulus) screened have an extremely low number of 577 XX individuals. Thus, the screening of ACTN3 in negroid African populations (and, likely, the related West Africans and African-Americans) to detect 577XX genotypes may prove useful in identifying individuals with sprint/power potential. In one embodiment, a method for screening for an ACTN3 allele (e.g. 577R, 577X) alone or in combination with another screening methods may be used to select, or at least assist in the selection of, young individuals with elite sprint/power potential (e.g. potential as track sprinters, short distance swimmers, and track cyclists).

Other genes may also have beneficial effects on sprint/power and/or endurance athletic performance. For example, angiotensin-converting enzyme (ACE) is reported to have two alleles, I and D, which have an effect on athletic performance. The I allele is associated with lower ACE activity in both serum and tissue (Reider et al., "Sequence variation in the human angiotensin converting enzyme." Nat Genet, 1999 vol. 22 pp59-62). It is reported that there is an increased frequency of the I allele in elite endurance athletes (Gayagay et al. 1998 "Elite endurance athletes and the ACE I allele; the role of genes in athletic performance". Hum Genet 103:48-50; Montgomery et al. 1998 Human gene for physical performance. Nature 393:221-222; Myerson et al. 1999 Human angiotensin I-converting enzyme gene and endurance performance. J Appl Physiol 87:1313-1316; Nazarov et al. 2001 The angiotensin converting enzyme I/D polymorphism in Russian athletes Eur J Hum Genet 9:797-801). Conversely, an increased frequency of the ACE D allele has been associated with elite sprint performance (Myerson et al. 1999 Human angiotensin I-converting enzyme gene and endurance performance. J Appl Physiol 87:1313-1316; Nazarov et al. 2001 The angiotensin converting enzyme I/D polymorphism in Russian athletes Eur J Hum Genet 9:797-801; Woods et al. 2001 Elite swimmers and the D allele of the ACE I/D polymorphism. Hum Genet 108: 230-232).

It is possible that there is a tradeoff between sprint and endurance attributes that imposes limitations on the evolution of physical performance in humans and other vertebrates (Garland et al. 1990 "Heritability of locomotor performance and its correlates in a natural population" Experientia 46:530-533). This is supported by data from world-class decathletes, which demonstrate that performance in the 100-m sprint, shot-put, long-jump, and 110-m hurdles (relying on explosive power and fast fatigue-susceptible muscle fibers) is negatively correlated with performance in the 1,500-m race (requiring endurance and fatigue-resistant slow fiber activity). (Van Damme et al. 2002 Performance constraints in decathletes. Nature 415:755-756). This suggests that an individual may be predisposed toward specialist performance in only one of the two areas (sprint/power vs. endurance). In particular embodiments of the invention, screening tests for ACTN3 may be combined with one or more genetic tests for other performance associated genes. Such tests may include any gene that is known in the art to be associated with sprint/power and/or endurance performance (e.g., Rankinen et al. 2002 "The human gene map for performance and health-related fitness phenotypes: the 2001 update" Med. Sci. Sports Exerc. 34: 1219-33; Perusse et al. 2003, "The human gene map for performance and health-related fitness phenotypes: the 2002 update" Med. Sci. Sports Exerc. 35: 1248-1264 incorporated herein by reference in their entirety).

Two reports (Rankinen et al. 2002; Perusse et al. 2003) have summarized the results of studies of performance and health-related fitness phenotypes. A human performance and health-related fitness gene map is shown as FIG. 1 in the 2002 article. The map includes all gene entries and QTL (quantitative trait loci) that have shown associations or linkages with exercise-related phenotypes. The chromosomes and their regions are from the Gene Map of the Human Genome web site, the National Center for Biotechnology Information (NCBI), National Institutes of Health, Bethesda, Md. The loci abbreviations and full names of the genes of potential use in conjunction with ACTN3 screening are summarized in TABLE 4. In one embodiment, analysis of one or more of the genes referenced in TABLE 4 may be used in combination with the evaluation of the ACTN3 gene of an individual to predict the elite athletic potential of that individual.

TABLE 5 summarizes a study (Perusse et al., 2003) of alleles and genotype frequencies of the ADRA2A (Alpha-2A-adrenergic receptor) and ACE (Angiotensin 1 converting enzyme) genes between endurance athletes and sedentary controls. TABLE 5 illustrates the differences between endurance athletes and sedentary individuals. In one embodiment of the invention, the examination of the ACTN3 genotype of a potential elite athlete may be combined with the assessment of either the ADRA2A genotype and/or the ACE genotype in order to more accurately predict the athletic potential of an individual. In another embodiment, the assessment of the ACTN3 genotype of an athlete may be combined with the assessment of either the ADRA2A genotype and/or the ACE genotype and/or other physiological assessments (eg $VO_2$ max etc.) to customize a training regimen for the athlete.

Evolutionary Divergence of ACTN3 and ACTN2

Genotyping of non-human primates indicates that the 577X null mutation has likely arisen in humans. The mouse genome contains four orthologues which all map to evolutionarily conserved regions for the four human genes. Murine ACTN2 and ACTN3 are differentially expressed, spatially and temporally, during embryonic development, and in contrast to humans, α-actinin-2 expression does not completely overlap α-actinin-3 in postnatal skeletal muscle, suggesting independent function. Furthermore, sequence comparison of human, mouse and chicken α-actinin genes demonstrates that ACTN3 has been conserved over a long period of evolutionary time, implying a constraint on evolutionary rate imposed by continued function of the gene. These observations provide a real framework in which to test theoretical models of genetic redundancy as they apply to human populations as well as other animals (Mills et al Differential Expression of the Actin-binding Proteins, α-actinin-2 and -3, in Different Species: Implications for the Evolution of Functional Redundancy" 2001 Hum Mol Gene 13:1335-1346).

To determine the origin of the 577X allele (and the 523R allele, which occurs in strong linkage disequilibrium with 577X), 36 unrelated baboons (diverged from human lineage $25 \times 10^6$ years ago) and 33 unrelated chimpanzees (diverged from human lineage $5 \times 10^6$ years ago) were genotyped. All 69 non-human primates were homozygous for the "wild-type" alleles in exons 15 (523Q) and 16 (577R), suggesting that the polymorphisms originated after the separation of the human and chimpanzee lineages, or that they have a very low frequency in non-human primates (Mills et al 2001).

As for mice, the similarity between mouse ACTN2 and ACTN3 is the same as between human ACTN2 and ACTN3, i.e. 88% similar and 79% identical. The mouse proteins are collinear and have the same functional domains as the human proteins—an N-terminal actinin-binding domain, four central repeat domains and C-terminal EF-hands (Mills et al 2001).

There is only one skeletal muscle ACTN gene in the chicken, whereas the mouse genome contains four orthologues which all map to evolutionarily conserved syntenic regions for the four human genes. Sequence comparison between mouse and human ACTN2 and ACTN3 suggests that the evolution of the α-actinins has been slow relative to other genes. The low rate of substitution in ACTN3 appears not to be due to an intrinsically low mutation rate in this gene (Mills et al 2001).

In other mammals, such as rabbits and pigs, there are also fast- and slow-muscle-specific isoforms of α-actinin, although the gene(s) responsible have not been isolated. The presence of two sarcomeric α-actinin genes may, however, be restricted to mammals.

In mammals both copies of the gene have survived, and the comparison of the human and mouse ACTN2 and ACTN3 sequences shows that the genes have been highly conserved throughout mammalian evolution (Mills et al 2001).

Elite Athletic Performance and Horses

The horse is one of very few animals besides some dogs and camels that is bred, kept or sold for its athletic performance and therefore is another model for studying gene expression as it correlates with performance. For example, the conservation of the ACTN3, an athletic marker in humans for athletic potential, and ACTN2 gene throughout species has been previously demonstrated. Although the equivalent gene has not yet been identified in horses, it is highly probable that a gene like ACTN3 exists in horses but has eluded detection. In certain embodiments of the invention, horses may be screened for an ACTN3-like gene. In other embodiments race horses such as the horses trained to compete in a derby may be screened for an ACTN3-like gene. Alternatively, horses required to sprint with enormous power such as polo ponies and barrel racing horses may also be screened for differential expression of an ACTN3-like gene. It is likely that the sprinting horses express a gene that is slightly different than an endurance horse and therefore analysis of the ACTN3-like gene may be an indicator of elite athletic potential in horses. Similar to what is seen in human athletes, screening a gene for a minor change, for example the presence or absence of a specific nucleotide sequence (eg. SNP site, deletion or insertion) may be a valuable indicator of elite athletic potential in an animal such as a horse. An ACTN3-like gene is a gene that has the same function as the ACTN3 in other species and/or it has sequence similarities to the ACTN3 gene.

Previous studies indicate the equine angiotensin-converting enzyme gene might be a candidate gene for athletic performance in horses. The human variant of the gene contains a polymorphic marker that is associated with increased athletic ability of elite endurance athletes and an increased anabolic response to training. (Ellis et al, Characterization of the Equine Angiotensin-converting Enzyme" 7th World Congress on Genetics Applied to Livestock Production, Aug. 19-23, 2002, Montpellier, France Session 05. Horse breeding Abstract of N° 05-07 GENE. N. A. I. Tammen, F. W. Nicholas and H. W. Raadsma. ReproGen, University of Sydney, Camden, Australia). To date, a correlation in horses of the ACE expression and elite athletic performance has been unsuccessful. Other studies including a study of the myosin heavy-chain gene(MyHC) in equine gluteus medius muscle where differential expression of the gene has been identified in foals but direct correlation of athletic abilities and presence or absence of the gene have not yet been correlated with performance (Eizema et al Differential Expression of Equine Myosin heavy-chain mRNA and Protein Isoforms in a Limb muscle" J Histochem Cytochem 2003 September; 51 (9): 1207-1216).

It is contemplated that the analysis of an ACTN3-like gene and other physiological and genetic parameters may be measured in horses in order to more accurately access the elite athletic ability of a horse at an early age. It is contemplated that horses may be pre-screened before using them for breeding purposes to identify a more satisfactory genetic match. In addition it is possible that a foal in utero may be screened in order to assess the athletic potential of the foal before it is born. The information generated from such screenings would save the breeders and investors of horses (camels, dogs) a tremendous amount of time and money as well as identify the potential ability of an animal at a early stage of development. As with humans, the information generated from genotypic screening of a horse as well as other parameters (bloodlines etc.) may help to identify a potential elite athlete and/or design a better training regiment for a specific animal (e.g., a polo pony).

Single Nucleotide Polymorphisms (SNPs)

Various embodiments of the invention provide for methods for determining a correlation between a polymorphism or genetic variation (e.g, a SNP) and a phenotype, comprising: a) providing: samples from one or more subjects; possibly medical records from one or more subjects, for determining a phenotype of the subject(s) and detection assays that detect a polymorphism; b) exposing the samples to detection assays under conditions such that the presence or absence of at least one polymorphism is revealed; and; c) determining a correlation between the at least one polymorphism and the phenotype of the subjects.

Nucleic acids in the region of interest (e.g., the region containing the genetic variation of interest) may be assayed using any suitable method, including but not limited to manual sequencing using radioactive marker nucleotides, or automated sequencing. The sequence may be examined and the presence or absence of a given SNP or mutation determined. The particular SNP site(s) (e.g. 1747 C>T of ACTN3) of a gene may be used to evaluate the presence, absence or change in a particular gene in order to assess the athletic potential of an individual or modify a training regimen for that individual. The known SNPs for ACTN3 are listed in TABLE 3. In various embodiments of the invention, screening for the 1747 C>T SNP of the ACTN3 gene may be combined with screening for any other known polymorphism in the ACTN3 gene, including but not limited to any SNP listed in TABLE 3.

Other SNPs of potential use in the practice of the claimed methods are disclosed for example, in the Table of published U.S. patent application Ser. No. 801274, publication No. 20020032319, incorporated herein by reference in its entirety. Any one or more of these sites may be assayed in combination with 1747 C>T SNP of the ACTN3 gene to predict the athletic potential of an individual, select or match a sport or sporting event to an individual's chances of success) and/or to optimize a training regimen.

In alternative embodiments of the invention, screening for genetic variations may utilize other detection assays, such as an allele-specific hybridization assay. In a hybridization assay, the presence of absence of a given SNP or other genetic variation is determined based on the ability of the DNA from the sample to hybridize to a complementary DNA molecule (e.g., a oligonucleotide probe). A variety of hybridization assays using a variety of techniques for hybridization and detection are known in the art and any such known technique may be used in the claimed methods. Exemplary assays are disclosed below.

In some embodiments, detection assays may utilize a DNA chip hybridization assay. In such assays, a series of oligonucleotide probes are affixed to a solid support. In some embodiments, the oligonucleotide probes are designed to be unique to a given SNP or mutation. The DNA sample of interest is contacted with the DNA "chip" and hybridization is detected. DNA chips, including customized DNA chips specific for particular SNP sequences, are available from commercial sources such as Affymetrix (Santa Clara, Calif.).

In other exemplary embodiments, polymorphisms may be detected using a SNP-IT primer extension assay (Orchid Biosciences, Princeton, N.J.; e.g., U.S. Pat. Nos. 5,952,174 and 5,919,626). In this assay, SNPs are identified by using a specially synthesized DNA primer and a DNA polymerase to selectively extend the DNA chain by one base at the suspected SNP location. DNA in the region of interest is amplified and denatured. Polymerase reactions are then performed using microfluidic systems. Detection is accomplished by adding a label to the nucleotide suspected of being at the SNP or mutation location. Incorporation of the label into the DNA can be detected by any suitable method (e.g., if the nucleotide contains a biotin label, detection is via a fluorescently labelled antibody specific for biotin). Other commercial kits may be used to identify the presence or absence of one or more SNPs (e.g., Applied Biosystems: SNaPSOT, Assay-on-Demand, Assay-By-Design, Pyrosequencing assays.

Nucleic Acids

Various embodiments of the invention involve the isolation and analysis of nucleic acid molecules, such as DNA, mRNA or cDNA. Nucleic acids of interest may encode a portion or all of a targeted protein (eg ACTN3, ACE etc.). A "nucleic acid" as used herein includes single-stranded and double-stranded molecules, as well as DNA, RNA, chemically modified nucleic acids and nucleic acid analogs. It is contemplated that a nucleic acid within the scope of the present invention may be of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, about 110, about 120, about 130, about 140, about 150, about 160, about 170, about 180, about 190, about 200, about 210, about 220, about 230, about 240, about 250, about 275, about 300, about 325, about 350, about 375, about 400, about 425, about 450, about 475, about 500, about 525, about 550, about 575, about 600, about 625, about 650, about 675, about 700, about 725, about 750, about.775, about 800, about 825, about 850, about 875, about 900, about 925, about 950, about 975, about 1000, about 1100, about 1200, about 1300, about 1400, about 1500, about 1750, about 2000, about 2250, about 2500 or greater nucleotide residues in length, up to and including full-length chromosomal DNA.

Methods for partially or fully purifying DNA and/or RNA from complex mixtures, such as cell homogenates or extracts, are well known in the art. (See, e.g., *Guide to Molecular Cloning Techniques*, eds. Berger and Kimmel, Academic Press, New York, N.Y., 1987; *Molecular Cloning: A Laboratory Manual*, 2nd Ed., eds. Sambrook, Fritsch and Maniatis, Cold Spring Harbor Press, Cold Spring Harbor, N.Y., 1989). Generally, cells, tissues or other source material containing nucleic acids are first homogenized, for example by freezing in liquid nitrogen followed by grinding in a mortar and pestle. Certain tissues may be homogenized using a Waring blender, Virtis homogenizer, Dounce homogenizer or other homogenizer. Crude homogenates may be extracted with detergents, such as sodium dodecyl sulphate (SDS), Triton X-100, CHAPS (3-[(3-cholamidopropyl)-dimethylammonio]-1-propane sulfonate), octylglucoside or other detergents known in the art. As is well known, nuclease inhibitors such as RNase or DNase inhibitors may be added to prevent degradation of target nucleic acids.

Extraction may also be performed with chaotrophic agents such as guanidinium isothiocyanate, or organic solvents such as phenol. In some embodiments, protease treatment, for example with proteinase K, may be used to degrade cell proteins. Particulate contaminants may be removed by centrifugation or ultracentrifugation. Dialysis against aqueous buffer of low ionic strength may be of use to remove salts or other soluble contaminants. Nucleic acids may be precipitated by addition of ethanol at $-20°$ C., or by addition of sodium acetate (pH 6.5, about 0.3 M) and 0.8 volumes of 2-propanol. Precipitated nucleic acids may be collected by centrifugation or, for chromosomal DNA, by spooling the precipitated DNA on a glass pipet or other probe. The skilled artisan will realize that the procedures listed above are exemplary only and that many variations may be used, depending on the particular type of nucleic acid to be analyzed.

In certain embodiments, nucleic acids to be analyzed may be naturally occurring DNA or RNA molecules. Virtually any naturally occurring nucleic acid may be analyzed by the disclosed methods including, without limit, chromosomal, mitochondrial or chloroplast DNA or ribosomal, transfer, heterogeneous nuclear or messenger RNA. Nucleic acids may be obtained from either prokaryotic or eukaryotic sources by standard methods known in the art. Alternatively, nucleic acids of interest may be prepared artificially, for example by PCR™ or other known amplification processes or by preparation of libraries such as BAC, YAC, cosmid, plasmid or phage libraries containing nucleic acid inserts. (See, e.g., Berger and Kimmel, 1987; Sambrook et al., 1989.) The source of the nucleic acid is unimportant for purposes of analysis and it is contemplated within the scope of the invention that nucleic acids from virtually any source may be analyzed.

Nucleic Acid Amplification

In particular embodiments, nucleic acids to be analyzed for screening may first be amplified to increase the signal strength. Nucleic acid sequences to be used as a template for amplification may be isolated from cells contained in a biological sample (eg DNA or mRNA from skeletal muscle), according to standard methodologies. The nucleic acid may be genomic DNA or fractionated or whole cell RNA. Where RNA is used, it may be desired to convert the RNA to a complementary cDNA. In one embodiment, the RNA is whole cell RNA and is used directly as the template for amplification. In one example, the determination of the ACTN3 genotype is performed by amplifying (e.g. by PCR) the ACTN3 polynucleotide sequences, or more preferably a fragment thereof which includes the 1747 C>T SNP (e.g. exon 16), and sequencing the amplification products or otherwise detecting the presence and/or absence of the 1747 C>T SNP in the amplification products. In another example, it is known that the 577X allele contains a DdeI restriction site which can be readily detected by DdeI digestion of the amplification products and size fractionation of the digestion products (e.g. by gel electrophoresis). The size of the products may be used to genotype the ACTN3 locus in the individual.

Various forms of amplification are well known in the art and any such known method may be used. Generally, amplification involves the use of one or more primers that hybridize selectively or specifically to a target nucleic acid sequence to be amplified.

Primers

The term primer, as defined herein, is meant to encompass any nucleic acid that is capable of priming the synthesis of a nascent nucleic acid in a template-dependent process. Typically, primers are oligonucleotides from ten to twenty base pairs in length, but longer sequences may be employed. Primers may be provided in double-stranded or single-stranded form, although the single-stranded form is preferred. Methods of primer design are well-known in the art, based on the design of complementary sequences obtained from standard Watson-Crick base-pairing (i.e., binding of adenine to thymine or uracil and binding of guanine to cytosine). Computerized programs for selection and design of amplification primers are available from commercial and/or public sources well known to the skilled artisan. Particular primer sequences of use in detecting genetic variants predictive of athletic performance, such as the 1747 C>T SNP in ACTN3, are provided in the following Examples. The skilled artisan will realize that the specific sequences provided are exemplary only and that alternative primer and/or probe sequences may be used in the practice of the claimed methods.

Amplification Methods

A number of template dependent processes are available to amplify the marker sequences present in a given sample. One of the best known amplification methods is the polymerase chain reaction (referred to as PCR) which is described in detail in U.S. Pat. Nos. 4,683,195, 4,683,202 and 4,800,159.

One embodiment of the invention may comprise obtaining a suitable sample from an individual and detecting a specific messenger RNA, such as an ACTN3 mRNA. An exemplary sample for use in this method is a muscle tissue sample (e.g. muscle tissue biopsy, such as a punch biopsy). Once the tissue sample is obtained the sample may be prepared for isolation of the nucleic acids by standard techniques (eg single cell isolation, digestion of outer membranes, Oligo dT isolation of mRNA etc.) The isolation of the mRNA may also be performed using kits known to the art (Pierce, AP Biotech, etc). A reverse transcriptase PCR amplification procedure may be performed in order to quantify an amount of mRNA amplified. Methods of reverse transcribing RNA into cDNA are well known and described in Sambrook et al., 1989. Alternative methods for reverse transcription utilize thermostable DNA polymerases. These methods are described in WO 90/07641 filed Dec. 21, 1990.

Another method for amplification of nucleic acids is the ligase chain reaction ("LCR"), disclosed in European Application No. 320 308. In LCR, two complementary probe pairs are prepared, and in the presence of the target sequence, each pair will bind to opposite complementary strands of the target such that they abut. In the presence of a ligase, the two probe pairs will link to form a single unit. By temperature cycling, as in PCR, bound ligated units dissociate from the target and then serve as "target sequences" for ligation of excess probe pairs. U.S. Pat. No. 4,883,750 describes a method similar to LCR for binding probe pairs to a target sequence.

Qbeta Replicase, described in PCT Application No. PCT/US87/00880, may also be used as still another amplification method in the present invention. In this method, a replicative sequence of RNA that has a region complementary to that of a target is added to a sample in the presence of an RNA polymerase. The polymerase will copy the replicative sequence that may then be detected.

An isothermal amplification method, in which restriction endonucleases and ligases are used to achieve the amplification of target molecules that contain nucleotide 5'-[alpha-thio]-triphosphates in one strand of a restriction site may also be useful in the amplification of nucleic acids in the present invention (Walker et al., Proc. Nat'l Acad. Sci. USA 89:392-396, 1992).

Strand Displacement Amplification (SDA) is another method of carrying out isothermal amplification of nucleic acids which involves multiple rounds of strand displacement and synthesis, i.e., nick translation. A similar method, called Repair Chain Reaction (RCR), involves annealing several probes throughout a region targeted for amplification, followed by a repair reaction in which only two of the four bases are present. The other two bases may be added as biotinylated derivatives for easy detection. A similar approach is used in SDA. Target specific sequences may also be detected using a cyclic probe reaction (CPR). In CPR, a probe having 3' and 5' sequences of non-specific DNA and a middle sequence of specific RNA is hybridized to DNA which is present in a sample. Upon hybridization, the reaction is treated with RNase H, and the products of the probe identified as distinctive products which are released after digestion. The original template is annealed to another cycling probe and the reaction is repeated.

Still other amplification methods described in GB Application No. 2 202 328, and in PCT Application No. PCT/US89/01025 may be used in accordance with the present invention. In the former application, "modified" primers are used in a PCR like, template and enzyme dependent synthesis. The primers may be modified by labelling with a capture moiety (e.g., biotin) and/or a detector moiety (e.g., enzyme). In the latter application, an excess of labelled probes are added to a sample. In the presence of the target sequence, the probe binds and is cleaved catalytically. After cleavage, the target sequence is released intact to be bound by excess probe. Cleavage of the labelled probe signals the presence of the target sequence.

Other nucleic acid amplification procedures include transcription-based amplification systems (TAS), including nucleic acid sequence based amplification (NASBA) and 3SR. Kwoh et al., Proc. Nat'l Acad. Sci. USA 86:1173 (1989); Gingeras et al., PCT Application WO 88/10315. In NASBA, the nucleic acids may be prepared for amplification by standard phenol/chloroform extraction, heat denaturation of a clinical sample, treatment with lysis buffer and minispin columns for isolation of DNA and RNA or guanidinium chloride extraction of RNA. These amplification techniques involve annealing a primer which has target specific sequences. Following polymerization, DNA/RNA hybrids are digested with RNase H while double stranded DNA molecules are heat denatured again. In either case the single stranded DNA is made fully double stranded by addition of second target specific primer, followed by polymerization. The double-stranded DNA molecules are then multiply transcribed by a polymerase such as T7 or SP6. In an isothermal cyclic reaction, the RNA's are reverse transcribed into double stranded DNA, and transcribed once against with a polymerase such as T7 or SP6. The resulting products, whether truncated or complete, indicate target specific sequences.

Davey et al., European Application No. 329 822 disclose a nucleic acid amplification process involving cyclically synthesizing single-stranded RNA ("ssRNA"), ssDNA, and double-stranded DNA (dsDNA), which may be used in accordance with the present invention. The ssRNA is a first template for a first primer oligonucleotide, which is elongated by reverse transcriptase (RNA-dependent DNA polymerase). The RNA is then removed from the resulting DNA:RNA duplex by the action of ribonuclease H (RNase H, an RNase specific for RNA in duplex with either DNA or RNA). The resultant ssDNA is a second template for a second primer, which also includes the sequences of an RNA polymerase promoter (exemplified by T7 RNA polymerase) 5' to its homology to the template. This primer is extended by DNA polymerase (exemplified by the large "Klenow" fragment of E. coli DNA polymerase I), producing a double-stranded DNA ("dsDNA") molecule with a sequence identical to that of the original RNA between the primers and having additionally, at one end, a promoter sequence. This promoter sequence may be used by the appropriate RNA polymerase to make many RNA copies of the DNA. These copies may then re-enter the cycle leading to very swift amplification. With proper choice of enzymes, this amplification may be done isothermally without addition of enzymes at each cycle. Because of the cyclical nature of this process, the starting sequence may be chosen to be in the form of either DNA or RNA.

Miller et al., PCT Application WO 89/06700 disclose a nucleic acid sequence amplification scheme based on the hybridization of a promoter/primer sequence to a target single-stranded DNA ("ssDNA") followed by transcription of many RNA copies of the sequence. This scheme is not cyclic, i.e., new templates are not produced from the resultant RNA transcripts. Other amplification methods include "race" and "one-sided PCR." Frohman, M. A., In: *PCR PROTOCOLS: A GUIDE TO METHODS AND APPLICATIONS*, Academic Press, N.Y. (1990) and Ohara et al., *Proc. Nat'l Acad. Sci. USA*, 86:5673-5677 (1989).

Methods based on ligation of two (or more) oligonucleotides in the presence of nucleic acid having the sequence of the resulting "di-oligonucleotide", thereby amplifying the di-oligonucleotide, may also be used in the amplification step of the present invention. (e.g., Wu et al., *Genomics* 4:560 1989).

Separation Methods

Following amplification, it may be desirable to separate the amplification product from the template and the excess primer for the purpose of determining whether specific amplification has occurred. In one embodiment, amplification products are separated by agarose, agarose-acrylamide or polyacrylamide gel electrophoresis using standard methods. (E.g., Sambrook et al., 1989) Alternatively, chromatographic techniques may be employed to effect separation. There are many kinds of chromatography which may be used in the present invention (Freifelder, 1982).

Identification Methods

Various methods for detection of nucleic acid sequence variants are known in the art and any such known method may be used. In one embodiment, detection may be by Southern blotting and hybridization with a labelled probe. The techniques involved in Southern blotting are well known to those of skill in the art (e.g., Sambrook et al., 1989). Briefly, amplification products are separated by gel electrophoresis. The gel is then contacted with a membrane, such as nitrocellulose, permitting transfer of the nucleic acid and non-covalent binding. Subsequently, the membrane is incubated with a chromophore-conjugated probe that is capable of hybridizing with a target amplification product. Detection is by exposure of the membrane to x-ray film or ion-emitting detection devices. One example of the foregoing is disclosed in U.S. Pat. No. 5,279,721, which shows an apparatus and method for the automated electrophoresis and transfer of nucleic acids. The apparatus permits electrophoresis and blotting without external manipulation of the gel and is suited for carrying out methods according to the present invention.

Methods and apparatus for detecting nucleic acid sequence variants are commercially available from a variety of sources, such as Third Wave, Pyrosequencing, Applied Biosystems, Affymetrix, Sequenom, Nanogen and others and any such commercial system may be used to detect sequence variants in ACTN3 or other performance related genes.

Proteins and Peptides

In certain embodiments, the disclosed methods may involve detecting and/or quantifying the amount of a specific protein (e.g. ACTN3) in samples to be screened. For convenience, the terms "protein," "polypeptide" and "peptide are used interchangeably herein. Although a variety of methods of protein quantification are known in the art and may be used, antibody-based assays, such as ELISA, are particularly useful for protein quantification. The skilled artisan will realize that the following discussion is exemplary only and that any known techniques for protein identification/quantification may be used.

In certain embodiments a protein or peptide may be isolated or purified. Protein purification techniques are well known to those of skill in the art. These techniques involve, at one level, the homogenization and crude fractionation of the cells, tissue or organ to polypeptide and non-polypeptide fractions. The protein or polypeptide of interest may be further purified using chromatographic and electrophoretic techniques to achieve partial or complete purification (or purification to homogeneity). Analytical methods particularly suited to the preparation of a pure peptide are ion-exchange chromatography, gel exclusion chromatography, HPLC (high performance liquid chromatography) FPLC (AP Biotech), polyacrylamide gel electrophoresis, affinity chromatography, immunoaffinity chromatography and isoelectric focusing. An example of receptor protein purification by affinity chromatography is disclosed in U.S. Pat. No. 5,206,347, the entire text of which is incorporated herein by reference. One of the more efficient methods of purifying peptides is fast performance liquid chromatography (FPLC) or even HPLC.

A purified protein or peptide is intended to refer to a composition, isolatable from other components, wherein the protein or peptide is purified to any degree relative to its naturally-obtainable state. An isolated or purified protein or peptide, therefore, also refers to a protein or peptide free from the environment in which it may naturally occur. Generally, "purified" will refer to a protein or peptide composition that has been subjected to fractionation to remove various other components, and which composition substantially retains its expressed biological activity. Where the term "substantially purified" is used, this designation will refer to a composition in which the protein or peptide forms the major component of the composition, such as constituting about 50%, about 60%, about 70%, about 80%, about 90%, about 95%, or more of the proteins in the composition.

In certain embodiments, the disclosed methods may involve purifying one or more proteins or peptides. It may be of use when purifying a protein or a DNA sample that magnetic beads be used (Dynal, Dyna beads) to isolate the molecule and subsequently identify or quantitate the amount of molecule in a sample the molecule. These techniques are known by those skilled in the art.

Antibodies

In certain embodiments, it may be desirable to make antibodies against particular proteins or peptides of interest (e.g.

ACTN3). The appropriate protein, or portions thereof, may be conjugated, or chemically linked to one or more agents to enhance their immunogenicity, as is well known in the art. Preferred agents are the carriers are keyhole limpet hemocyanin (KLH) or bovine serum albumin (BSA).

In one embodiment, the detection of a targeted protein may be by Western blot or immunocytochemistry using one or more specific antibodies to all or a portion of a target protein (e.g. ACTN3) with a specific antibody or fragment thereof (e.g. Fab fragment or a recombinant antibody fragment such as a scFv). One example of an antibody that may be used is anti-ACTN3 antibodies (as disclosed in North, K. N. et al., *Neuromuscular Disorders*, 6, 229-235, 1996). In another embodiment, the level of a targeted protein may be detected by obtaining a sample from an individual (e.g. a muscle biopsy) and exposing the sample to one or more antibodies directed to the targeted protein.

The term "antibody" is used to refer to any antibody-like molecule that has an antigen binding region, and includes antibody fragments such as Fab', Fab, F(ab')$_2$, single domain antibodies (DABs), Fv, scFv (single chain Fv), and the like. Techniques for preparing and using various antibody-based constructs and fragments are well known in the art. Means for preparing and characterizing antibodies are also well known in the art (See, e.g., Harlow and Lane, Antibodies: A Laboratory Manual, Cold Spring Harbor Laboratory, 1988; incorporated herein by reference).

ELISA

In certain preferred embodiments, the amount of a protein of interest, such as ACTN3, may be determined by various types of enzyme linked immunosorbent assays (ELISAs) or radioimmunoassays (RIA) known in the art. Immunohistochemical detection using tissue sections is also particularly useful. However, it will be readily appreciated that detection is not limited to such techniques, and Western blotting, dot blotting, FACS analyses, and the like may also be used.

In one exemplary ELISA, antibodies binding to the target proteins (e.g. ACTN3) are immobilized onto a selected surface exhibiting protein affinity, such as a well in a microtiter plate. A test composition suspected of containing the protein or portion of the protein is introduced to the well. After binding and washing to remove non-specifically bound immune complexes, the bound antigen (protein of interest) may be detected. Detection is generally achieved by the addition of a second antibody specific for the target protein that is linked to a detectable label. This type of ELISA is a "sandwich ELISA". Detection may also be achieved by the addition of a second antibody, followed by the addition of a third antibody that has binding affinity for the second antibody, with the third antibody being linked to a detectable label.

In another exemplary ELISA, the samples suspected of containing the protein (antigen) are immobilized onto the well surface and then contacted with the antibodies of the invention. After binding and washing to remove non-specifically bound immune complexes, the bound antigen is detected. Where the initial antibodies are linked to a detectable label, the immune complexes may be detected directly. Alternatively, the immune complexes may be detected using a second antibody that has binding affinity for the first antibody, with the second antibody being linked to a detectable label.

Another ELISA in which the proteins or peptides are immobilized, involves the use of antibody competition in the detection. In this ELISA, labelled antibodies are added to the wells, allowed to bind to the target protein, and detected by means of their label. The amount of target antigen in an unknown sample is then determined by mixing the sample with the labelled antibodies before or during incubation with coated wells. The presence of target antigen in the sample acts to reduce the amount of antibody available for binding to the well and thus reduces the ultimate signal. This is appropriate for detecting antibodies in an unknown sample, where the unlabelled antibodies bind to the antigen-coated wells and also reduces the amount of antigen available to bind the labelled antibodies.

In coating a plate with either antigen or antibody, one will generally incubate the wells of the plate with a solution of the antigen or antibody, either overnight or for a specified period of hours. The wells of the plate will then be washed to remove incompletely adsorbed material. Any remaining available surfaces of the wells are then "coated" with a nonspecific protein that is antigenically neutral with regard to the test antisera. These include bovine serum albumin (BSA), casein and solutions of milk powder. The coating allows for blocking of nonspecific adsorption sites on the immobilizing surface and thus reduces the background caused by nonspecific binding of antisera onto the surface.

In ELISAs, it is more customary to use a secondary or tertiary detection means rather than a direct procedure. Thus, after binding of a protein or antibody to the well, coating with a non-reactive material to reduce background, and washing to remove unbound material, the immobilizing surface is contacted with the control biological sample to be tested under conditions effective to allow immune complex (antigen/antibody) formation. Detection of the immune complex then requires a labelled secondary binding ligand or antibody, or a secondary binding ligand or antibody in conjunction with a labelled tertiary antibody or third binding ligand.

"Under conditions effective to allow immune complex (antigen/antibody) formation" means that the conditions preferably include diluting the antigens and antibodies with solutions such as BSA, bovine gamma globulin (BGG) and phosphate buffered saline (PBS)/Tween. These added agents also tend to assist in the reduction of nonspecific background.

The "suitable" conditions mean that the incubation is at a temperature and for a period of time sufficient to allow effective binding. Incubation steps are typically from about 1 to 2 to 4 hours, at temperatures preferably on the order of 25 C to 27 C, or may be overnight at about 4 C or so.

Following all incubation steps in an ELISA, the contacted surface is washed so as to remove non-complexed material. A preferred washing procedure includes washing with a solution such as PBS/Tween, or borate buffer. Following the formation of specific immune complexes between the test sample and the originally bound material, and subsequent washing, the occurrence of even minute amounts of immune complexes may be determined.

To provide a detecting means, the second or third antibody will have an associated label to allow detection. Preferably, this will be an enzyme that will generate color development upon incubating with an appropriate chromogenic substrate. Thus, for example, one will desire to contact and incubate the first or second immune complex with a urease, glucose oxidase, alkaline phosphatase or hydrogen peroxidase-conjugated antibody for a period of time and under conditions that favor the development of further immune complex formation (e.g., incubation for 2 hours at room temperature in a PBS-containing solution such as PBS-Tween).

After incubation with the labelled antibody, and subsequent to washing to remove unbound material, the amount of label is quantified, e.g., by incubation with a chromogenic substrate such as urea and bromocresol purple or 2,2'-azido-di-(3-ethyl-benzthiazoline-6-sulfonic acid [ABTS] and $H_2O_2$, in the case of peroxidase as the enzyme label. Quantitation is then achieved by measuring the degree of color generation (e.g., using a visible spectra spectrophotometer).

Kits

In still further embodiments, the present invention concerns detection kits for use with the nucleic acid or immunodetection methods described above. Depending upon the type of assay to be utilized, a kit may comprise one or more primer pairs for amplification of a target nucleic acid sequence, one or more probes, such as labelled probes, to detect a genetic variant, and one or more control target sequences to confirm amplification and/or probe binding conditions. Controls may include, for example, specific target sequences for each allele of the 1747 C>T SNP in ACTN3. Probes may also be specific for hybridization to the 1747 C>T SNP alleles. Various other reagents of use, such as buffer, nucleotides, and polymerase may also be included.

In kits for immunoassay of protein, immunodetection kits may comprise, in suitable container means, a target protein or peptide, or a first antibody that binds to a target protein or peptide, and an immunodetection reagent. The kits may comprise a first antibody specific for the target protein or peptide and a labelled second antibody specific for the first antibody. Alternatively, kits may comprise a first and a second antibody specific or selective for a protein of interest, with the second antibody labelled. Alternatively, the first and second antibody may be unlabelled and a third antibody, specific for the second antibody, may be included. Other standard reagents, such as buffer and various substrates or reactants used to develop a labelled antibody may also be included.

The container means of the kits will generally include at least one vial, test tube, flask, bottle, syringe or other container means, into which a sample may be placed, and preferably, suitably aliquoted. Where a second or third binding ligand or additional component is provided, the kit will also generally contain a second, third or other additional container into which this ligand or component may be placed. Such kits may include injection or blow-molded plastic containers into which the desired vials are retained.

Performance Testing

In certain embodiments, the screening methods of use may include, in addition to ACTN3 assays, one or more performance based tests. Such performance tests may be used in combination with, for example, ACTN3 SNP testing or ACTN3 protein or mRNA assays. Various exemplary performance tests are discussed below. The skilled artisan will realize that the examples are not limiting and any performance assay known in the art may be used.

$VO_2$ Max Testing $VO_2$ max testing provides athletes with a direct measure of their physiological potential. Maximum oxygen consumption rates under conditions of vigorous exercise are determined by methods well known in the art. Data includes aerobic and anaerobic thresholds, heart rate and speed, ventilatory parameters, maximum heart rate and heart rate zones.

Anaerobic Threshold Testing (Blood Lactate & Ventilatory)

Anaerobic Threshold refers to the point in exercise where lactic acid production is equal to removal. This intensity is equivalent to a 60-120 min run or cycle depending on fitness, technique and experience. The test is conducted by simultaneously measuring ventilation as well as blood lactate levels. Although the ventilatory and blood lactate methods produce very similar results, they both accurately determine anaerobic threshold. Information provided by this test include blood lactate threshold and ventilatory threshold, heart rates at anaerobic threshold and speed (run) or watts (cycle) at anaerobic threshold Anaerobic Power and Capacity Testing (Wingate Test)

The Wingate test determines leg power and capacity and is designed for power sport athletes. The test is a 30 second all out effort on a cycle ergometer that determines peak power and ability to resist fatigue. Data collected from a Wingate test includes: (30 s test) peak power (watts), absolute, relative and fatigue index (how fast power drops off over the 30 s test) and work (joules) (energy expenditure).

Critical Power (CP)

The goal of CP tests is to determine what is the optimal workload that an athlete can sustain for a given time period or distance. The most common CP tests may include CP (60-180s), time frame dependant on sport; and CP Time Trial.

Resting Metabolic Rate (RMR)

RMR is also referred to as Resting Energy Expenditure (REE). It is a non-invasive method of determining the minimal amount of calories (Kcal) an individual utilizes in a day. The higher the RMR, the more calories an individual burns. The results are directly measured by O2 and CO2 inspiration and expiration. One test protocol consists of no food or alcohol for 12 hours, no stimulants for 24 hours such as coffee and no exercise for 24-36 hours. The test is most commonly recommended for early in the morning. The individual is connected to a metabolic measuring machine for 30 min while lying on his back in a rested state. During the test, the individual breathes into the metabolic measuring machine through a mouthpiece and fitted hose. At the completion of the test, the following information is gathered: Metabolic Rate (RMR)–Kcal/day·Respiratory Rate (RR), Respiratory Exchange Ratio (RER), Ventilation and heart rate at rest % of Carbohydrates and Fat utilized at rest Speed/Power Testing Speed/Power Testing consists most commonly of three tests: Running Speed: Infrared Timing Lights (5-50 meters); a Vertical Jump & Leg Power: Vertec apparatus and Agility Tests: Standard and Sport Specific. These tests assist in the analysis of an individuals capabilities in, for example, power sports).

Strength/Flexibility Testing

Strength/Flexibility testing generally consists of RM (resting muscle) strength: squat, bench, dead-lift, leg press; Muscular Endurance: repeated repetitions at a specified weight; Olympic Lifts: Clean & Jerk, Snatch, Power Cleans, Power Snatch; Flexibility: standard and sport-specific and abdominal and lower back strength.

Body Composition

A body composition test may consist of a Harpenden skinfold caliper test (pinching the skin in several sites on the body such as under the arm, hip etc.) and estimating the percent body fat as well as estimating lean muscle mass and fat mass. Another method involves immersion in water in a tank with deflated lungs. Body fat is measured by a special measuring device that determines water displacement.

Applicability of Methods

While the disclosed methods are suitable for the prediction of athletic performance in sprint/power-type sports and events in Caucasian individuals, the methods may also be suitable for use in any other ethnic group which generally shows a high frequency (i.e. preferably at least 5%, more preferably at least 10%, and most preferably at least 15%) of the 577XX genotype. After analyzing multiple Caucasians and several other ethnic groups, the null genotype if absent from an individual athlete such as the Zulus and certain Caucasian females appears to correlate with the potential to be a sprint/power elite athlete versus an endurance athlete. For example, the null genotype is common within the Native American population (29%), Asian population (25%) and White Europeans (20%), PNG Highlanders (15%), African American population (13%) and the Aboriginal Australian population (10%).

Talent search programs may utilize the methods of the present invention by themselves or in combination with similar methods for genotyping individuals in respect of other genes linked to athletic performance. Other methods that may be combined with the methods disclosed are based upon performance data and phenotypic predictors (eg. height and build) and the like. Thus, the results of the methods of the present invention may be used to select, or at least assist in the selection of, young individuals with elite athlete potential and/or to provide guidance on the type of sport that a young individual may choose to specialize.

In another embodiment, training programs may be devised for a potential or current elite athlete that have greater chance of success, based on the knowledge of genetic factors that will predict a person's training capability (e.g. levels of ACTN3 protein or mRNA and/or SNP detection). Individualized training programs may focus on specific talents (determined from genetic makeup) by identifying the type of training that is most likely to be successful. This would help to narrow the small margin between success and failure at the elite level, avoid unnecessary fatigue from excessive training without the expected gains (eg. the genetic potential is not there); reduce wasted resources and premature "burn out"; and may enhance long-term goals and self esteem in an individual athlete. Resources are wasted every time an individual with elite athlete potential is removed from a program because he/she cannot achieve success. At a personal level, the effort and sacrifices already undertaken by such individuals can adversely affect their life goals and self esteem. In these situations, knowledge of the genetic makeup alone or in combination with other predictors may help to clarify why success has not been achieved, and will assist in directing the individual to more realistic life goals that may include a more appropriate sport.

Therefore, in one embodiment, identifying an improved training program for an athlete may involve the determination of a specific genotype of a targeted gene (e.g. ACTN3 genotype) of an athlete. Another example of developing a training program for a potential or current athlete may involve combining one or more tests for a targeted molecule with other performance assessing tests as indicated previously and analyzing the results of the two or more tests to develop a program.

EXAMPLES

Example 1

Screening for the ACTN3 Null (577XX) Genotype in Elite Athletes

Materials and Methods

Human genomic DNA was isolated from blood from a pool of elite athletes (108 endurance athletes and 83 sprint athletes), 88 African Zulu individuals and 152 control Australian Caucasian individuals, by phenol:chloroform extraction following cell lysis with Triton-X100 and digestion with proteinase K. Exon 16 of ACTN3 was amplified from genomic DNA. The primers corresponding to adjacent intronic sequences for exon 16 were:

```
forward   5'CTGTTGCCTGTGGTAAGTGGG3'   (SEQ ID NO: 1)
reverse   5'TGGTCACAGTATGCAGGAGGG3'   (SEQ ID NO: 2)
```

The PCR reaction cycle for the primers was: 35 cycles at 94° C. for 30s and then 72° C. for 1 min, with a final extension of 94° C. for 10 min. The R577X alleles (codons CGA and TGA respectively) can be distinguished by the presence (577X) or absence (577R) of a Dde I (C↓TNAG) restriction site in Exon 16. 577R (wild type) PCR products have 205 bp and 86 bp fragments; while 577X PCR products have 108 bp, 97 bp and 86 bp fragments. Digested PCR fragments were separated by 10% polyacrylamide gel electrophoresis and visualized by staining with ethidium bromide.

Results and Discussion

Results of the genotyping assays are shown in Table 2. ACTN3 genotyping was conducted in elite athletes (i.e. individuals who perform at the highest levels in terms of endurance, speed and/or strength). Compared to controls, elite sprint athletes had a low frequency of the ACTN3 null mutation 577XX (6% versus 18% in a control Caucasian population; p<0.05), similar to the trend observed in the Zulu population. Since, the force-generating capacity of type 2 muscle fibers at high velocity, the speed and tempo of movements, and the capacity of the individual to adapt to exercise training, all appear to be strongly genetically influenced, it is considered that ACTN3 genotype is likely to be a factor influencing normal variation in muscle function in the general population. Based on these results, ACTN3 genotyping is shown to be of considerable potential in the selection, or at least to assist in the selection, of young individuals with elite athletic potential.

Example 2

Methods 436 unrelated Caucasian controls were genotyped from three different sources (150 blood donors, 71 healthy children participating in an unrelated study, and 215 healthy adults participating in a talent-identification program with the Australian Institute of Sport), through use of the genotyping methodology described by Mills et al. (2001). Sex was known for 292 female controls and 134 male controls. 429 elite Caucasian athletes were genotyped from 14 different sports. For the purposes of the example, Athletes were defined as "elite" if they had represented Australia in their sport at the international level; 50 of the athletes had competed in Olympic Games.

Given the localization of α-actinin-3 in fast skeletal-muscle fibers, it was hypothesized that deficiency of α-actinin-3 would reduce performance in sprint/power events and would therefore be less frequent in elite sprint athletes. To test this hypothesis, the genotypes of a subset of 107 elite athletes (72 male and 35 female) were analyzed, classified a priori as specialist sprint/power athletes, blinded to genotyping results. This group comprised 46 track athletes competing in events of 800 m, 42 swimmers competing in events of 200 m, 9 judo athletes, 7 short-distance track cyclists, and 3 speed skaters. For comparison, a subset of 194 subjects (122 male and 72 female) classified independently as specialist endurance athletes and analyzed, including 77 long-distance cyclists, 77 rowers, 18 swimmers competing over distances of 400 m, 15 track athletes competing in events of 5,000 m, and 7 cross-country skiers. Thirty-two sprint athletes (25 male and 7 female) and 18 endurance athletes (12 male and 6 female) had competed at the Olympic level. Because of the stringency of the classification criteria, 128 of the elite athletes could not be unambiguously assigned into either the sprint/power or endurance groups and were excluded from subsequent analyses.

To test for homogeneity of ACTN3 allele and genotype frequencies between athlete and control groups, the log-linear modeling approach was used as described by Huttley and Wilson (2000), implemented in the statistical programming language R (version 1.6.2), through use of a package (contributed by J. Maindonald; available from The R Project for Statistical Computing Web site). "X" 2 values were estimated using genotype numbers for comparisons between athletes and controls. The genotypic profiles of the three control groups (150 blood donors, 71 healthy children, and 215 healthy adults) did not differ significantly from one another ($x^2$=0.19; P=0.996) nor from a previously genotyped group of 107 white Europeans (Mills et al. 2001), suggesting that the genotype frequencies in the control cohort are representative of a broader Caucasian population. ACTN3 genotype frequencies did not vary significantly between male and female control subjects, and, overall, there was no significant deviation from Hardy-Weinberg (H-W) equilibrium.

ACTN3 genotyping data from the control, sprint/power, and endurance groups are summarized in TABLE 2 and FIG. 1. There were no significant allele or genotype frequency differences between the elite athlete group as a whole and the controls. However, when the athletes were divided into sprint/power and endurance groups and compared with controls, there was strong evidence of allele frequency variation ($x^2_{[df=5]}$=23; P<0.001) There were significant allele frequency differences between sprint athletes and controls for both males ($x^2_{[df=1]}$=14.8; P<0.001) and females ($x^2_{[df=1]}$=7.2; P<0.01). Sprint athletes had a lower frequency of the 577XX (α-actinin-3 null) genotype (6% vs. 18%), and no female elite sprint athletes or sprint Olympians were 577XX. The sprint athlete group also had a higher frequency of the 577RR genotype (50% vs. 30%) and a lower frequency of the heterozygous 577RX genotype (45% vs. 52%), compared with controls. Elite endurance athletes had a slightly higher frequency of the 577XX genotype (24%) than did controls (18%). More importantly, allele frequencies in sprint and endurance athletes deviated in opposite directions and differed significantly from each other in both males ($x^2_{[df=1]}$=13.3; P<0.001) and females ($x^2_{[df=1]}$=5.8; P<0.05). The differences between the two groups effectively cancelled each other out, explaining the lack of association when the entire elite athletic cohort was compared with the control group.

Overall, there was also evidence of genotype variation that is not explained by allele frequency differences ($x^2_{[df=5]}$=16.7; P<0.01). This suggested variation in H-W disequilibrium coefficients among groups, despite there being no evidence for departure from H-W equilibrium overall. The effect was restricted to female sprint ($x^2_{[df=1]}$=7.4; P<0.01) and endurance ($x^2_{[df=1]}$=6.0; P<0.05) athletes, with more heterozygous female sprint athletes than expected at H-W equilibrium (20 vs. 15) and fewer than expected heterozygous female endurance athletes (25 vs. 36). The allele-frequency-independent genotype differences between female sprint and endurance athletes were highly significant ($x^2_{[df=1]}$=13.8; P<0.001). No effect was seen in males, suggesting that the effect of ACTN3 genotype on performance differs between males and females.

These findings suggest that the ACTN3 577R allele provides an advantage for power and sprint activities. No female elite sprint athletes in the sample were α-actinin-3 deficient (compared with 8% of males). In males, the androgen hormone response to training is likely to make a significant contribution to improvements in performance, so that the relative effect of α-actinin-3 on muscle power may be reduced. Interestingly, all male Olympian power athletes in the cohort had at least one copy of the functional 577R allele of ACTN3 (associated with the presence of α-actinin-3 in skeletal muscle), suggesting that "every variable counts" at the highest levels of sporting competition. Although at least 73 genetic loci have been associated with fitness and performance phenotypes (Rankinen et al. 2002 "The human gene map for performance and health-related fitness phenotypes: the 2001 update". Med Sci Sports Exerc 34:1219-1233), ACTN3 is the first structural skeletal-muscle gene for which such an association has been demonstrated.

The α-actinin-3 protein may promote the formation of fast-twitch fibers or alter glucose metabolism in response to training. In addition, α-actinin-3 may be evolutionarily optimized for the minimization of damage caused by eccentric muscle contraction. The Z line in fast, glycolytic fibers is the structure most vulnerable to exercise-induced injury resulting in morphological damage and degradation of associated proteins, including the α-actinins (Friden and Lieber 2001, "Eccentric exercise-induced injuries to contractile and cytoskeletal muscle fiber components Acta Physiol Scand 171:321-326).

If the 577XX genotype enhances endurance performance as the 577R allele appears to enhance sprint-ability, then the 577R and 577X alleles may be maintained in the population because they both confer selective advantages under different environmental conditions and are thus kept at high population frequencies by balancing selection.

Example 3

FIG. 1 represents a histogram compilation of ACTN3 genotype frequency in controls, elite sprint/power athletes, and endurance athletes. Compared with healthy Caucasian controls, there is a marked reduction in the frequency of the ACTN3 577XX genotype (associated with α-actinin-3 deficiency) in elite Caucasian sprint athletes; remarkably, none of the female sprint athletes or sprint athletes who had competed at the Olympic level (25 males and 7 females) were α-actinin-3 deficient. Conversely, there is a trend toward an increase in the 577XX genotype in endurance athletes, although this association reaches statistical significance only in females. Error bars indicate 95% CIs.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

All of the COMPOSITIONS, METHODS and APPARATUS disclosed and claimed herein can be made and executed without undue experimentation in light of the present disclosure. While the compositions and methods of this invention have been described in terms of preferred embodiments, it are apparent to those of skill in the art that variations may be applied to the COMPOSITIONS, METHODS and APPARATUS and in the steps or in the sequence of steps of the methods described herein without departing from the concept, spirit and scope of the invention. More specifically, it are apparent that certain agents that are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

TABLE 1

Number and Frequency (%) of ACTN3 Genotypes and Frequency (%) of ACTN3 Alleles In Controls and Elite Sprint/Power and Endurance Athletes

| GROUP (n) | NO. (%) WITH GENOTYPE | | | ALLELE FREQUENCY (%) | |
|---|---|---|---|---|---|
| | RR | RX | XX | R | X |
| Male: | | | | | |
| Controls (134) | 40 (30) | 73 (54) | 21 (16) | 57 | 43 |
| Sprint (72) | 38 (53) | 28 (39) | 6 (8) | 72 | 28 |
| Endurance (122) | 34 (28) | 63 (52) | 25 (20) | 54 | 46 |
| Female: | | | | | |
| Controls (292) | 88 (30) | 147 (50) | 57 (20) | 55 | 45 |
| Sprint (35) | 15 (43) | 20 (57) | 0 (0) | 71 | 29 |
| Endurance (72) | 26 (36) | 25 (35) | 21 (29) | 53 | 47 |
| Total: | | | | | |
| Controls (436) | 130 (30) | 226 (52) | 80 (18) | 36 | 44 |
| Sprint (107) | 53 (50) | 48 (45) | 6 (6) | 72 | 28 |
| Endurance (194) | 60 (31) | 88 (45) | 46 (24) | 54 | 46 |

TABLE 2

Genotyping of R577X In ACTN3 in Caucasians Elite Athletes.

| Strength | Sport | ID | Sport Institute | Total Number | 577RR (%) | 577RX (%) | 577XX (%) |
|---|---|---|---|---|---|---|---|
| Endurance | Rower | RT492-RT556 | AIS | 64 | 22 (34.4%) | 28 (43.8%) | 14 (21.8%) |
| Endurance | Triathioner | RT977-RT989 | AIS | 13 | 3 (23.1%) | 8 (61.5%) | 2 (15.4%) |
| Endurance | Cyclist | RT990-RT998 | AIS | 9 | 4 (44.4%) | 2 (22.2%) | 3 (33.3%) |
| Endurance | Track Cyclist | KN246-KN275 | AIS | 22 | 7 (31.8%) | 7 (31.8%) | 8 (364%) |
| Endurance | Marathon | KN310 | AIS | 1 | 0 | 0 | 1 |
| Endurance | All above | | AIS | 108 | 36 (33.3%) | 45 (41.7%) | 27 (25.0%) |
| Sprint | Swimmer | RT901-RT1018 | AIS | 45 | 17 (37.8%) | 25 (55.6%) | 3 (6.6%) |
| Sprint | Track Cyclist | KN246-KN275 | AIS | 8 | 4 (50.0%) | 3 (37.5%) | 1 (12.5%) |
| Sprint | Athletics | KN276-KN309 | AIS | 30 | 16 (53.3%) | 13 (43.3%) | 1 (3.3%) |
| Sprint | All above | | AIS | 83 | 37 (44.6%) | 41 (49.4%) | 5 (6.0%) |
| Africa Zulu | | | | 88 | 69 (78.4%) | 18 (20.5%) | 1 (1.1%) |
| Australian Caucasian Control | | | | 152 | 46 (30.0%) | 78 (52.0%) | 28 (18%) |

TABLE 3

SNPs identified in the ACTN3 gene to date
NCBI SNP CLUSTER ID rs2229456
rs2229455
rs2229454
rs2228325
rs1126675
rs7949754
rs7924602
rs5792393
rs4990284
rs4990283
rs4013815
rs3937320
rs3837428
rs3814736
rs3814735
rs3782080
rs2511217
rs2511216
rs2509559
rs2509558
rs2305537
rs2305534
rs2290463
rs2275998
rs2096583
rs2000939
rs1815739
rs1791690
rs1671064
rs679228
rs678397
rs677488
rs647476
rs647029
rs618838
rs607736
rs597626
rs544021
rs540874
rs538330
rs531490
rs509556
rs490998
rs13897
rs4576
rs1189338
rs1201433
rs640213
rs3737525
rs3178740
rs3180065
rs3180064
rs3180063
rs3867132
rs608504
rs610293
rs3825065

TABLE 4

Symbols, full names, and cytogenic location of nuclear and mitochoncirial genes of the 2002 Human Gene Map for Performance and Health-Related fitness Phenotypes.

Gene or Locus Name Location

A B
ACADYL Acyl coenzyme A dehydrogenase, very long chain 1.7p13-p11
ACE Angiotensin I converting enzyme 17q23
ADRA2A Alpha-2A-adrenergic receptor 10q24-q26
ADRB1 Adrenergic, beta-1-, receptor 10q24-q26
ADRB2 Beta-2-adrenergic receptor 5q31-q32
ADRB3 Beta-3-adrenergic receptor 8p12-p11.2

TABLE 4-continued

Symbols, full names, and cytogenic location of nuclear and mitochoncirial genes of the 2002 Human Gene Map for Performance and Health-Related fitness Phenotypes.

Gene or Locus Name Location

AGT Angiotensinogen 1q42-q43
ANG Angiogenin, ribonuclease, RNase A family, 5 14q11.1-q11.2
APOE Apolipoprotein E 19q13.2
ATP1A2 ATPase, Na_/K_ transporting, alpha-2 polypeptide 1q21-q23
ATP1B1 ATPase, Na_/K_ transporting, beta 1 polypeptide 1q22-q25
BDKRB2 Bradykinin receptor B2 14q32.1-32.2
C D E F G
CASQ2 Calsequestrin 2 (cardiac muscle) 1p13.3-p11
CFTR Cystic fibrosis transmembrane conductance regulator, ATP-binding cassette (sub-family C, member 7) 7q31.2
CKM Creatine kinase, muscle 19q13.2-q13.3
CNTF Ciliary neurotrophic factor 11q12.2
CPT2 Carnitine palmitoyltransferase 2 1p32
COL1A1 Collagen, type I, alpha I 17q21.3-q22.1
EDN1 Endothelin 1 6p24.1
ENO3 Enolase 3, (beta, muscle) 17pter-p11
FABP2 Fatty acid binding protein 2 4q28-q31
FGA Fibrinogen, A alpha polypeptide 4q28
FGB Fibrinogen, B beta polypeptide 4q28
GDF8 (MSTN) Growth differentiation factor 8 (myostatin) 2q32.2
GNB3 Guanine nucleotide binding protein (G protein), beta polypeptide 3 12p13
H I K L M
HLM-A Major histocompatibility complex, class I, A 6p21.3
HP Haptoglobin 16q22.1
IGF1 Insulin-like growth factor I 12q22-q23
IGF2 Insulin-like growth factor 2 11p15.5
IL-6 Interleukin-6
KCNQ1 K_voltage-gated channel, KQT-like subfamily, member 1 11p15.5
LDHA Lactate dehydrogenase A 11p15.4
LPL Lipoprotein lipase 8p22
MTCO1 Cytochrome c oxidase I mtDNA 5904-7445
MTCO3 Cytochrome a oxidase III mtDNA 9207-9990
MTCYB Cytochrome b mtDNA 14747-15887
MTND1 NADH dehydrogenase I mtDNA 3307-4262
MTND4 NADH dehydragenase 4 mtDNA 10760-12137
MTND5 NADH dehydrogenase 5 mtDNA 12337-14148
MTTE Transfer RNA, mitochondrial, glutamic acid mtDNA 14674-14742
MTTI Transfer RNA, mitochondrial, isoleucine mtDNA 4263-4331
MTTK Transfer RNA, mitochondrial, lysine mtDNA 8295-8364
MTTL1 Transfer RNA, mitochondrial, leucine 1 (UUR) mtDNA 3230-3304
MTTL2 Transfer RNA, mitochondrial, leucine 2 (CUN) mtDNA 12266-12336
MTTM Transfer RNA, mitochondrial, methionine mtDNA 4402-4469
MTTT Transfer RNA, mitochondrial, threonine mtDNA 15888-15953
MTTY Transfer RNA, mitochondrial, tyrosine mtDNA 5826-5891
MyHC myosin Heavy-chain
N O P Q R S T U V
NOS3 Nitric oxide synthase 3 (endothelial cell) 7q36
NPY Neuropeptide Y 7p15.1
PAI1 Plasminogen activator inhibitor 1 7q21.3-q22
PFKM Phosphofructokinase, muscle 12q13.3
PGAM2 Phosphoglycerate mutase 2 (muscle) 7p13-p12
PGK1 Phosphoglycerate kinase 1 Xq13
PHKA1 Phosphorylase kinase, alpha 1 (muscle) Xq12-q13
PON1 Paraoxonase 1 7q21.3
PPARA Peroxisome proliferative activated receptor, alpha 22q13.31
PPARG Peroxisome proliferative activated receptor, gamma 3p25
PYGM Phosphorylase, glycogen, muscle 11q12-q13.2
RYR2 Ryanodine receptor 2 (cardiac) 1q42.1-q43
SGCA Sarcoglycan, alpha (50 kDa dystrophin-associated glycoprotein) 17q21

TABLE 4-continued

Symbols, full names, and cytogenic location of nuclear and mitochoncirial genes of the 2002 Human Gene Map for Performance and Health-Related fitness Phenotypes.

Gene or Locus Name Location

S100A1 S100 calcium binding protein Al 1q21
SUR Sulfonylurea receptor 11p15.1
TGFB1 Transfonriing growth factor beta 1 19q13.2
UCP2 Uncoupling protein 2 11q13
UCP3 Uncoupling protein 3 11q13
VDR Vitamin D (1,25-dihydroxyvitamin D3) receptor 12q12-q14

The gene symbols, names and cytogenetic locations are from the Locus Link web site available from the National Center for Biotechnology Information (NCBI). For mitochondrial DNA, locations are from the human mitochondrial genome data base.

TABLE 5

Endurance phenotypes and ease-control studies (DNA polymorphisms).

| Gene | Location | Athletes | | | Controls | | |
|---|---|---|---|---|---|---|---|
| | | N | Sports | Freq. | N | Freq. | P |
| ADRA2A | 10q24-q26 | 140 | Endurance | 6.7/6.7: 0.77 | 141 | 6.7/63: 0.62 | 0.037 |
| | | | | 6.7/6.3: 0.21 | | 6.7/6.3: 034 | |
| | | | | 6.3/6.3: 0.02 | | 6.3/6.3: 0.04 | |
| | | | | 6.7: 0.88 | | 6.7: 0.8 | 0.011 |
| | | | | 6.3: 0.12 | | 6.3: 0.2 | |
| ACE | 17q23 | 64 | Endurance | II: 0.30 | 118 | II: 0.18 | 0.03 |
| | | | | ID: 0.55 | | ID: 0.51 | |
| | | | | DD: 0.16 | | DD: 0.32 | |
| | | | | I: 0.57 | | I: 0.43 | 0.02 |
| | | | | D: 0.43 | | D: 0.57 | |
| | | 79 | Running | I: 0.57 | Ref. Pop. | I: 0.49 | 0.039 |
| | | | | D: 0.43 | | D: 0.51 | |
| | | 25 | Mountain-earing | NA | Ref. Pop. | NA | 0.02 / 0.003 |
| | | 60 | Elite athletes (cycling, running, handball) | II: 0.25 ID: 0.58 DD: 0.17 I: 0.54 D: 0.46 | Ref. Pop. | II: 0.16 ID: 0.45 DD: 0.39 I: 0.38 D; 0.62 | 0.0009 |
| | | 56 | Elite swimmers (sub-sample of 103 swimmers) | II: 0.15 ID: 0.39 DD: 0.46 I: 0.34 D: 0.66 | 1248 | II: 0.24 ID: 0.49 PD: 0.27 I: 0.48 D: 0.52 | 0.004 |

Reference: Perusse et at 2003 "The human gene map for performance and health-related fitness phenotypes: the 2002 update" Med. Sci. Sports Exerc. 35: 1248-1264.

TABLE 6

Genotype and allelic frequencies of ACTN3 577R/X alleles in human populations.

| Ethnic group | No. of chromosomes | No. of genotypes RX | No. of genotypes XX | Relative allele frequency of 577X |
|---|---|---|---|---|
| Asian | 56 | 14 | 7 | 0.5 ± 0.07 |
| Javanese | 96 | 28 | 12 | 0.54 ± 0.05 |
| Native American | 14 | 2 | 2 | 0.43 ± 0.14 |
| Asia/Americas | 166 | 44 | 21 | 0.52 ± 0.04 |
| Hispanic | 64 | 16 | 5 | 0.41 ± 0.06 |
| White | 214 | 47 | 21 | 0.42 ± 0.03 |
| Europe | 278 | 63 | 26 | 0.41 ± 0.03 |
| Aboriginal | 174 | 33 | 9 | 0.29 ± 0.09 |
| Australian | 78 | 16 | 6 | 0.36 ± 0.05 |
| PNG Highlander | | | | |
| Australasia | 252 | 49 | 15 | 0.31 ± 0.03 |
| African American | 90 | 12 | 6 | 0.27 ± 0.05 |
| African Bantu | 156 | 14 | 1 | 0.10 ± 0.05 |
| Africa | 246 | 56 | 7 | 0.16 ± 0.05 |
| Unknown | 152 | 50 | 11 | 0.47 |
| Total | 1094 | 232 | 80 | |

What is claimed is:

1. A method to predict potential sprinting, strength, or power performance in a human comprising:
   a) analyzing a sample obtained from the human for the presence of one or more genetic variations in α-actinin-3 (ACTN3) gene;
   b) detecting the presence of two 577R alleles at the loci encoding amino acid number 577 of the α-actinin-3 (ACTN3) protein; and
   c) predicting the potential sprinting, strength, or power performance of the human, wherein the presence of two copies of the 577R allele is positively associated with potential sprinting, strength, or power performance.

2. The method of claim 1, which comprises genotyping the human at the ACTN3 locus.

3. The method of claim 1, further comprising measuring the amount of ACTN3 protein present in the human's skeletal muscle.

4. The method of claim 3, wherein the amount of ACTN3 protein is measured using an antibody specific for the ACTN3 protein.

5. The method of claim 1, further comprising measuring the amount of ACTN3 messenger RNA (mRNA) expressed in the human's skeletal muscle.

6. The method of claim 1, further comprising identifying the 577R alleles in the human's genomic DNA by DNA sequencing, allele-specific hybridization, allele-specific amplification or restriction fragment length polymorphism analysis.

7. The method of claim 1, further comprising screening the human for the presence of one or more genetic variations in at least one other gene.

8. The method of claim 1, further comprising screening the human using a test selected from the group consisting of $VO_2$ maximum, anaerobic threshold test, Wingate test, critical power, resting metabolic rate, body composition, speed testing, power testing, strength testing, flexibility testing, muscle biopsy, fast twitch fiber test and slow twitch fiber test.

9. A method of selecting a training program based on potential sprinting, strength, or power performance for a human comprising:
   a) analyzing a sample obtained from the human for the presence of one or more genetic variations in α-actinin-3 (ACTN3) gene;
   b) detecting the presence of two 577R alleles at the loci encoding amino acid number 577 of the α-actinin-3 (ACTN3) protein;
   c) predicting the potential sprinting, strength, or power performance of the human, wherein the presence of two 577R alleles is positively associated with potential sprinting, strength, or power performance, and
   d) selecting a training program based on predicting potential sprinting, strength and power performance of step c).

10. A method of selecting a sprint/power sport or event based on potential sprinting strength and power performance for a human comprising:
   a) analyzing a sample obtained from the human for the presence of one or more genetic variations in α-actinin-3 (ACTN3) gene;

b) detecting the presence of two 577R allele at the loci encoding amino acid number 577 of the α-actinin-3 (ACTN3) protein;

c) predicting the potential sprinting, strength, or power performance of the human, wherein the presence of two 577R alleles is positively associated with potential sprinting, strength, or power performance, and d) selecting a sprint/power sport or event based on predicting potential sprinting, strength and power performance of step c).

11. The method of claim 1, wherein analyzing the sample further comprises analyzing DNA of the sample.

12. The method of claim 1, wherein the 577R allele is a SNP.

13. The method of claim 1, wherein the presence of a 577RR genotype is positively associated with potential sprinting, strength or power performance in males.

14. The method of claim 1, wherein the presence of a 577RR genotype is positively associated with potential sprinting, strength or power performance in females.

* * * * *

UNITED STATES PATENT AND TRADEMARK OFFICE
CERTIFICATE OF CORRECTION

| | | |
|---|---|---|
| PATENT NO. | : 7,615,342 B2 | Page 1 of 1 |
| APPLICATION NO. | : 10/527831 | |
| DATED | : November 10, 2009 | |
| INVENTOR(S) | : Kathryn Nance North | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 381 days.

Signed and Sealed this

Twenty-eighth Day of September, 2010

David J. Kappos
*Director of the United States Patent and Trademark Office*